(12) United States Patent
Cooke et al.

(10) Patent No.: US 6,926,725 B2
(45) Date of Patent: Aug. 9, 2005

(54) THROMBECTOMY DEVICE WITH MULTI-LAYERED ROTATIONAL WIRE

(75) Inventors: David Cooke, Groveland, MA (US); Suzanne W. George, Boston, MA (US)

(73) Assignee: Rex Medical, L.P., Conshohocken, PA (US)

(*) Notice: Subject to any disclaimer, the term of this patent is extended or adjusted under 35 U.S.C. 154(b) by 144 days.

(21) Appl. No.: 10/390,416

(22) Filed: Mar. 17, 2003

(65) Prior Publication Data
US 2003/0191483 A1 Oct. 9, 2003

Related U.S. Application Data
(60) Provisional application No. 60/369,953, filed on Apr. 4, 2002.

(51) Int. Cl.$^7$ .................................................. A61B 17/22
(52) U.S. Cl. ..................................................... 606/159
(58) Field of Search ................................. 606/159, 113, 606/114, 127, 170, 171, 176, 180; 600/585

(56) References Cited

U.S. PATENT DOCUMENTS

| | | |
|---|---|---|
| 2,756,752 A | 7/1956 | Scherlis |
| 3,108,594 A | 10/1963 | Glassman |
| 3,612,058 A | 10/1971 | Ackerman |
| 3,741,214 A | 6/1973 | Tillander |
| 3,749,085 A | 7/1973 | Willson et al. |
| 3,841,308 A | 10/1974 | Tate |
| 4,030,503 A | 6/1977 | Clark, III |
| 4,559,046 A | 12/1985 | Groshong et al. |
| 4,579,127 A | 4/1986 | Haacke |
| 4,614,188 A | 9/1986 | Bazell et al. |
| 4,646,736 A | 3/1987 | Auth |
| 4,664,112 A | 5/1987 | Kensey et al. |
| 4,676,778 A | 6/1987 | Nelson, Jr. |
| 4,706,671 A | 11/1987 | Weinrib |

(Continued)

FOREIGN PATENT DOCUMENTS

| | | |
|---|---|---|
| DE | 3640034 | 5/1988 |
| DE | 8900494 | 4/1989 |
| EP | 0452631 | 2/1991 |
| EP | 0709110 | 5/1996 |
| EP | 0815894 | 1/1998 |
| WO | WO 9923958 | 5/1999 |

OTHER PUBLICATIONS

"Bacchus Vascular Solera Thrombectomy Catheter Brochure" dated Jan. 4, 2002.

www.rexmedical.com—home page (Jul. 2000).

*Primary Examiner*—Kevin T. Truong
(74) *Attorney, Agent, or Firm*—Lerner, David, Littenberg, Krumholz & Mentlik, LLP

(57) ABSTRACT

An improvement to a thrombectomy apparatus for breaking up thrombus or other obstructive material in a lumen of a vascular graft or vessel having a wire and flexible sheath relatively movable, wherein the wire is sinuous in configuration and assumes its sinuous configuration when in the deployed configuration and has a straighter configuration in the first configuration. The wire is operatively connected to a motor for rotation of the wire to enable peaks of the sinuous wire to contact a wall of the lumen to break up the thrombus or other obstructive material. The improvement to the thrombectomy apparatus comprises the wire being formed of an inner core formed by a plurality of twisted wires and an outer wire wound directly around the inner core, wherein a distal portion of the outer wire extends distal of the inner core and progressively tapers towards a distal end to form a tapered region.

15 Claims, 8 Drawing Sheets

U.S. PATENT DOCUMENTS

| | | |
|---|---|---|
| 4,732,154 A | 3/1988 | Shiber |
| 4,745,919 A | 5/1988 | Bundy et al. |
| 4,794,928 A | 1/1989 | Kletschka |
| 4,819,634 A | 4/1989 | Shiber |
| 4,883,460 A | 11/1989 | Zanetti |
| 4,935,025 A | 6/1990 | Bundy et al. |
| 4,984,581 A | 1/1991 | Stice |
| 5,011,488 A | 4/1991 | Ginsburg |
| 5,024,651 A | 6/1991 | Shiber |
| 5,054,501 A | 10/1991 | Chuttani et al. |
| 5,069,662 A | 12/1991 | Bodden |
| 5,078,722 A | 1/1992 | Stevens |
| 5,078,723 A | 1/1992 | Dance et al. |
| 5,116,352 A | 5/1992 | Schnepp-Pesch et al. |
| 5,195,954 A * | 3/1993 | Schnepp-Pesch et al. ... 606/159 |
| 5,217,026 A | 6/1993 | Stoy et al. |
| 5,248,296 A | 9/1993 | Alliger |
| 5,250,060 A | 10/1993 | Carbo et al. |
| 5,251,640 A | 10/1993 | Osborne |
| 5,261,877 A | 11/1993 | Fine et al. |
| 5,269,751 A | 12/1993 | Kaliman et al. |
| 5,269,793 A | 12/1993 | Simpson |
| 5,313,967 A | 5/1994 | Lieber et al. |
| 5,334,211 A | 8/1994 | Shiber |
| 5,345,945 A | 9/1994 | Hodgson et al. |
| 5,370,653 A | 12/1994 | Cragg |
| 5,372,144 A | 12/1994 | Mortier et al. |
| 5,395,311 A | 3/1995 | Andrews |
| 5,403,334 A | 4/1995 | Evans et al. |
| 5,423,799 A | 6/1995 | Shiu |
| 5,423,838 A | 6/1995 | Willard |
| 5,484,412 A | 1/1996 | Pierpont |
| 5,488,958 A | 2/1996 | Topel et al. |
| 5,490,859 A | 2/1996 | Mische et al. |
| 5,497,782 A | 3/1996 | Fugoso |
| 5,514,092 A | 5/1996 | Forman et al. |
| 5,527,326 A | 6/1996 | Hermann et al. |
| 5,542,925 A | 8/1996 | Orth |
| 5,551,443 A | 9/1996 | Sepetka et al. |
| 5,562,275 A | 10/1996 | Weissenfluh et al. |
| 5,584,843 A | 12/1996 | Wulfman et al. |
| 5,599,307 A | 2/1997 | Bacher et al. |
| 5,605,162 A | 2/1997 | Mirzaee et al. |
| 5,630,823 A | 5/1997 | Schmitz-Rode et al. |
| 5,632,755 A | 5/1997 | Nordgren et al. |
| 5,653,722 A | 8/1997 | Kieturakis |
| 5,683,362 A | 11/1997 | Rowland et al. |
| 5,688,234 A | 11/1997 | Frisbie |
| 5,695,507 A | 12/1997 | Auth et al. |
| 5,695,508 A | 12/1997 | Chigogidze |
| 5,702,412 A | 12/1997 | Popov et al. |
| 5,702,413 A | 12/1997 | Lafontaine |
| 5,728,123 A | 3/1998 | Lemelson et al. |
| 5,733,296 A | 3/1998 | Rogers et al. |
| 5,746,758 A | 5/1998 | Nordgren et al. |
| 5,755,968 A | 5/1998 | Stone |
| 5,766,191 A | 6/1998 | Trerotola |
| 5,766,192 A | 6/1998 | Zacca |
| 5,776,153 A | 7/1998 | Rees |
| 5,830,156 A | 11/1998 | Ali |
| 5,833,631 A | 11/1998 | Nguyen |
| 5,833,644 A | 11/1998 | Zadno-Azizi et al. |
| 5,840,046 A | 11/1998 | Deem |
| 5,843,103 A * | 12/1998 | Wulfman ............ 606/159 |
| 5,876,413 A | 3/1999 | Fogarty et al. |
| 5,876,414 A | 3/1999 | Straub |
| 5,882,329 A | 3/1999 | Patterson et al. |
| 5,885,227 A | 3/1999 | Finlayson |
| 5,895,398 A | 4/1999 | Wensel et al. |
| 5,902,263 A | 5/1999 | Patterson et al. |
| 5,904,679 A | 5/1999 | Clayman |
| 5,910,364 A | 6/1999 | Miyata et al. |
| 5,916,166 A | 6/1999 | Reiss et al. |
| 5,919,163 A | 7/1999 | Glickman |
| 5,938,623 A | 8/1999 | Quiachon et al. |
| 5,941,869 A | 8/1999 | Patterson et al. |
| 5,947,985 A | 9/1999 | Imran |
| 5,954,737 A | 9/1999 | Lee |
| 5,971,991 A | 10/1999 | Sunderland |
| 5,972,019 A | 10/1999 | Engelson et al. |
| 5,984,877 A | 11/1999 | Fleischhacker, Jr. |
| 6,001,068 A | 12/1999 | Uchino et al. |
| 6,001,112 A | 12/1999 | Taylor |
| 6,004,279 A | 12/1999 | Crowley et al. |
| 6,019,736 A | 2/2000 | Avellanet et al. |
| 6,022,336 A | 2/2000 | Zadno-Azizi et al. |
| 6,022,363 A | 2/2000 | Walker et al. |
| 6,030,397 A | 2/2000 | Monetti et al. |
| 6,036,708 A | 3/2000 | Sciver |
| 6,056,721 A | 5/2000 | Shulze |
| 6,066,158 A | 5/2000 | Engelson et al. |
| 6,080,170 A | 6/2000 | Nash et al. |
| RE36,764 E | 7/2000 | Zacca et al. |
| 6,102,884 A | 8/2000 | Squitieri |
| 6,113,614 A | 9/2000 | Mears |
| 6,129,750 A | 10/2000 | Tockman et al. |
| 6,143,009 A | 11/2000 | Shiber |
| 6,146,396 A | 11/2000 | Konya et al. |
| 6,146,397 A | 11/2000 | Harkrider, Jr. |
| 6,152,909 A | 11/2000 | Bagaoisan et al. |
| 6,156,046 A * | 12/2000 | Passafaro et al. ........... 606/159 |
| 6,168,570 B1 | 1/2001 | Ferrera |
| 6,183,487 B1 | 2/2001 | Barry et al. |
| 6,185,449 B1 | 2/2001 | Berg et al. |
| 6,193,735 B1 | 2/2001 | Stevens |
| 6,203,561 B1 | 3/2001 | Ramee et al. |
| 6,206,898 B1 | 3/2001 | Honeycutt et al. |
| 6,217,595 B1 | 4/2001 | Shturman et al. |
| 6,231,588 B1 | 5/2001 | Zadno-Azizi |
| 6,238,405 B1 | 5/2001 | Findlay, III et al. |
| 6,251,086 B1 | 6/2001 | Cornelius et al. |
| 6,254,550 B1 | 7/2001 | McNamara et al. |
| 6,264,667 B1 | 7/2001 | McGuckin, Jr. |
| 6,270,509 B1 | 8/2001 | Barry et al. |
| 6,287,271 B1 | 9/2001 | Dubrul et al. |
| 6,299,623 B1 | 10/2001 | Wulfman |
| 6,322,572 B1 | 11/2001 | Lee |
| 6,371,928 B1 | 4/2002 | Mcfann et al. |
| 6,402,745 B1 | 6/2002 | Wilk |
| 6,454,775 B1 | 9/2002 | Demarais et al. |
| 6,454,779 B1 | 9/2002 | Taylor |
| 6,482,215 B1 | 11/2002 | Shiber |
| 6,485,500 B1 | 11/2002 | Kokish et al. |
| 6,663,613 B1 | 12/2003 | Evans et al. |
| 2002/0165567 A1 | 11/2002 | Shiber |

* cited by examiner

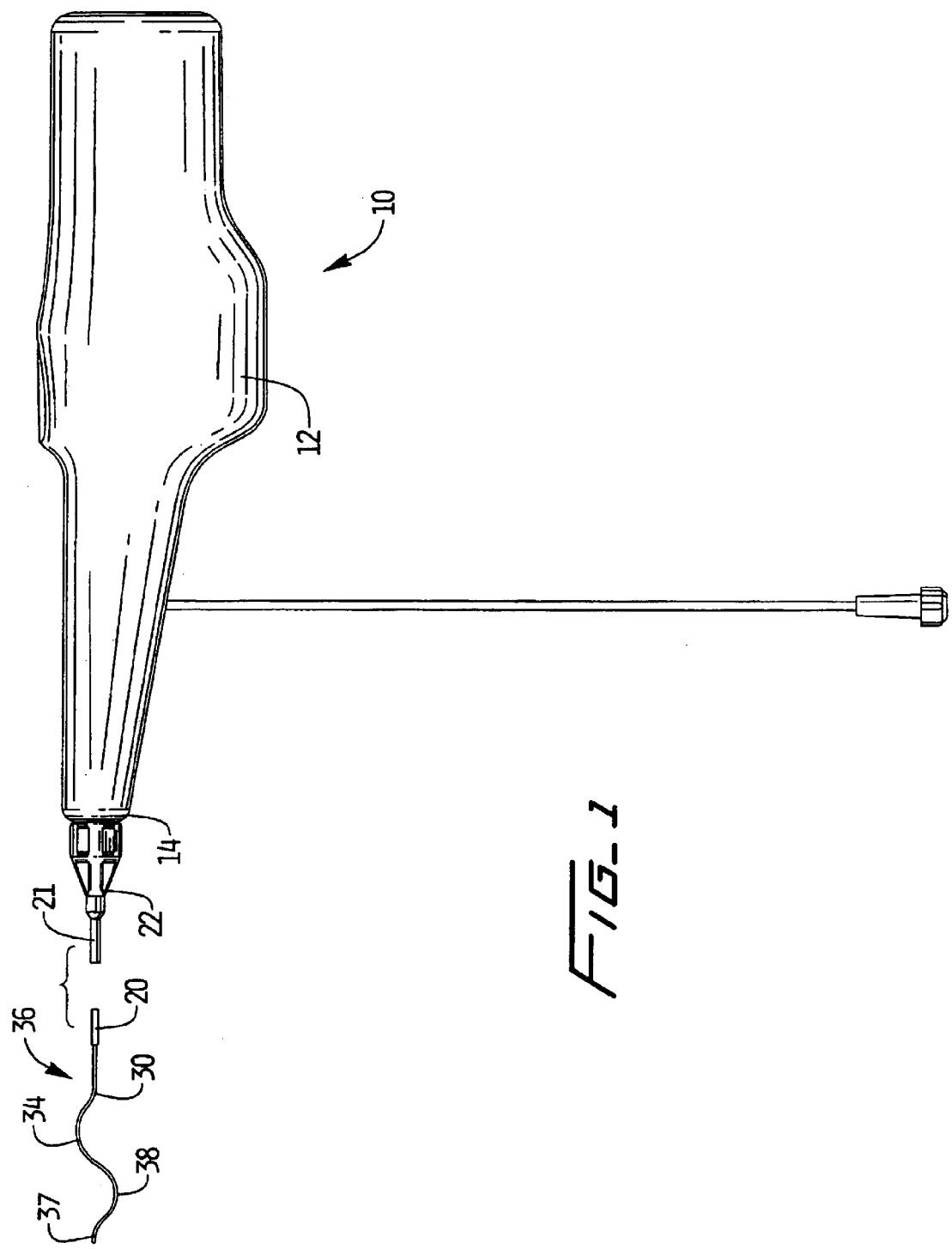

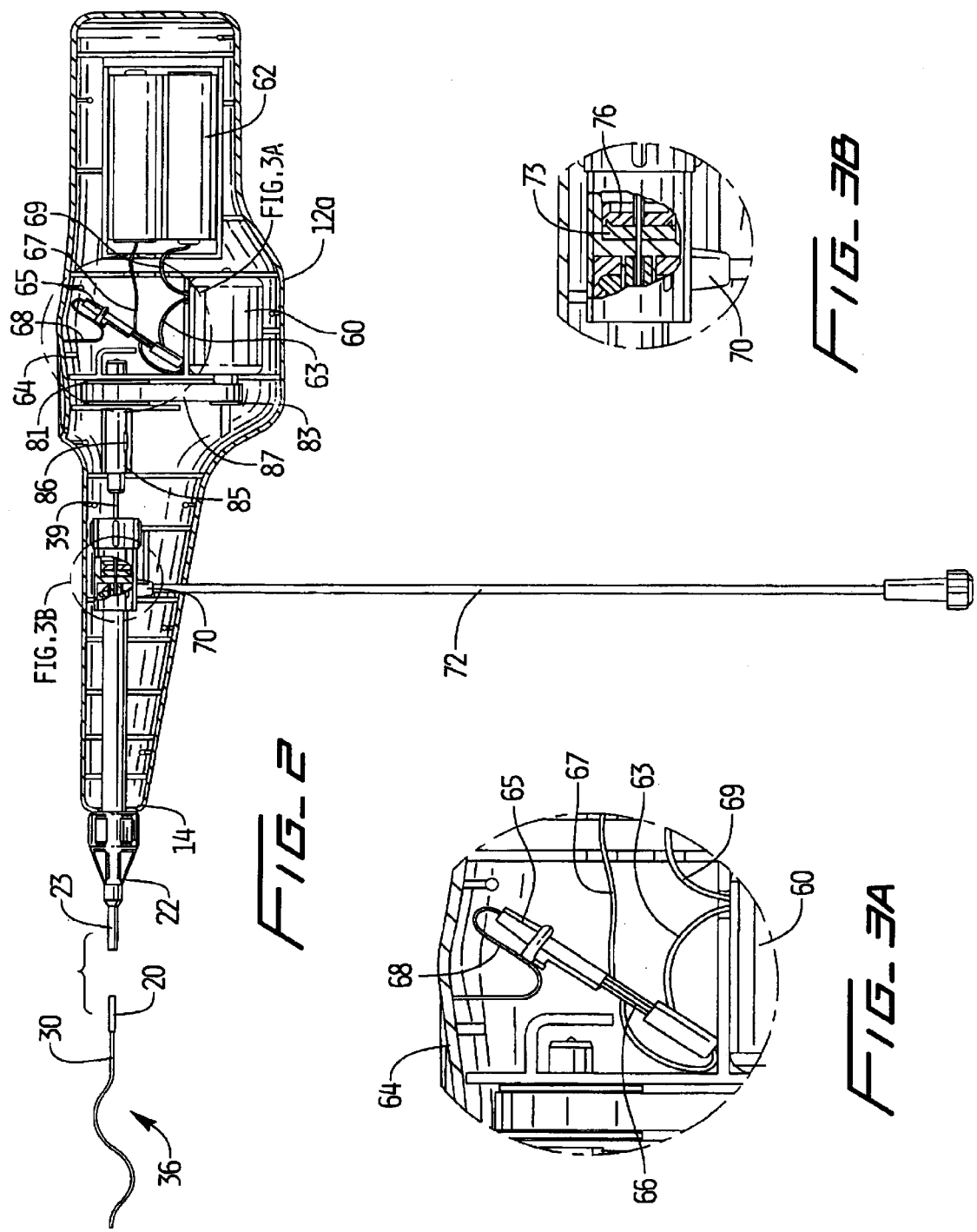

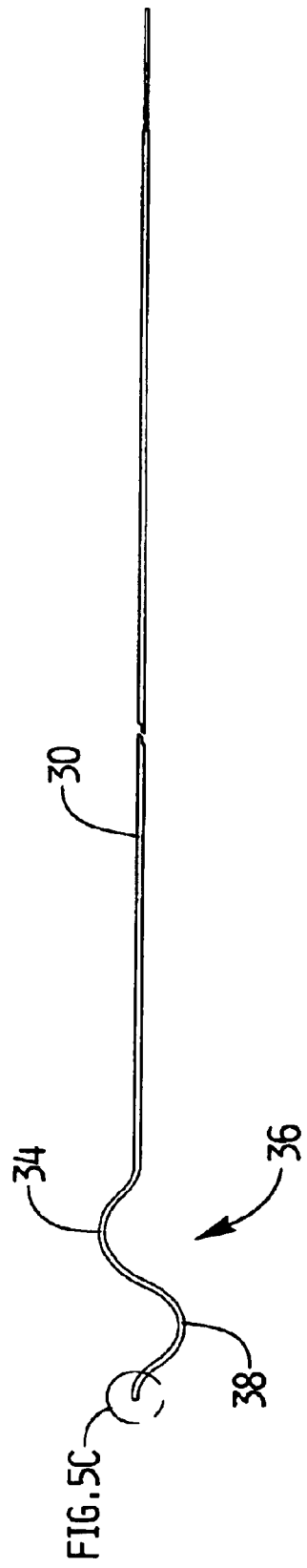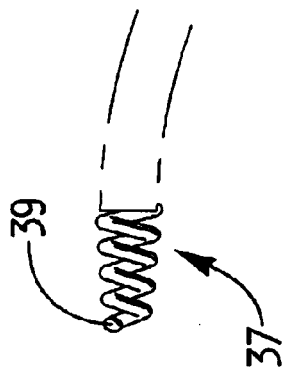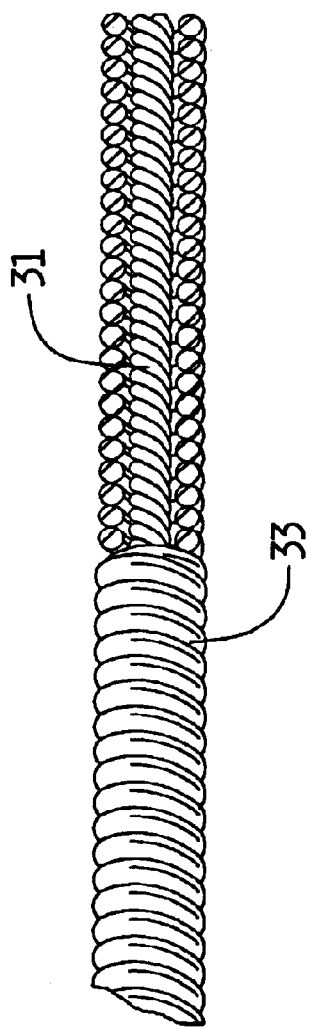

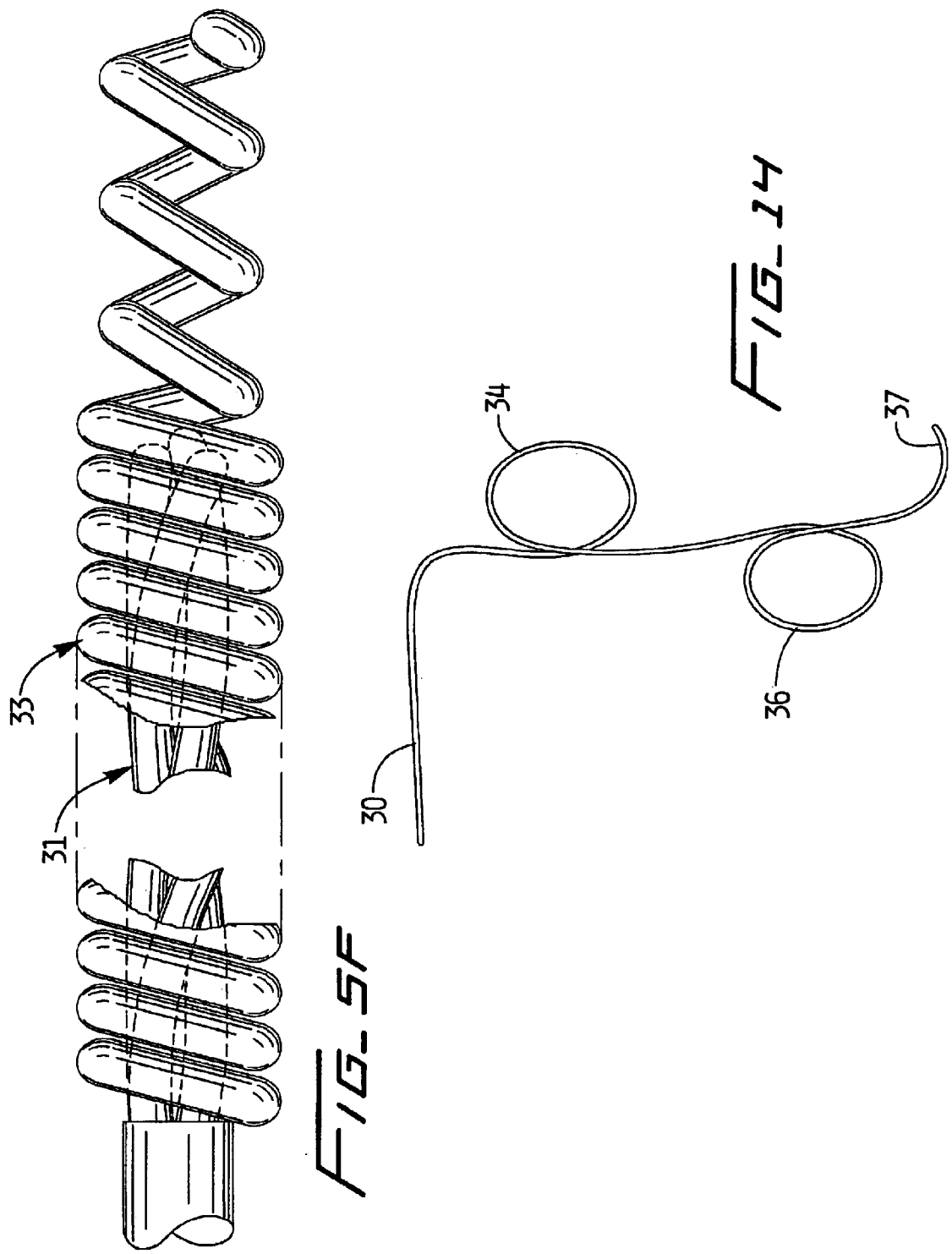

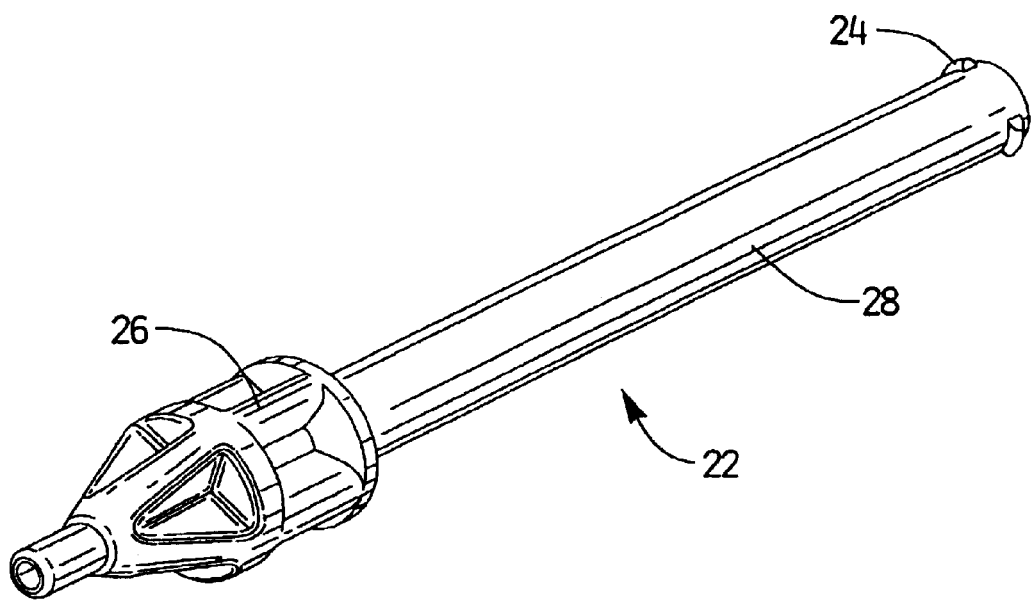
FIG_6
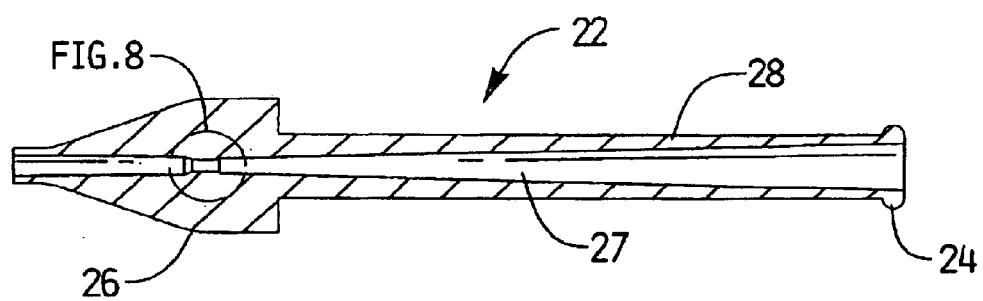
FIG_7
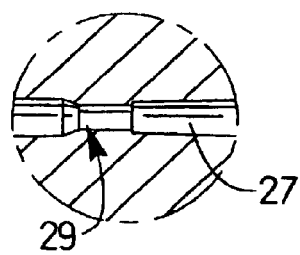
FIG_8

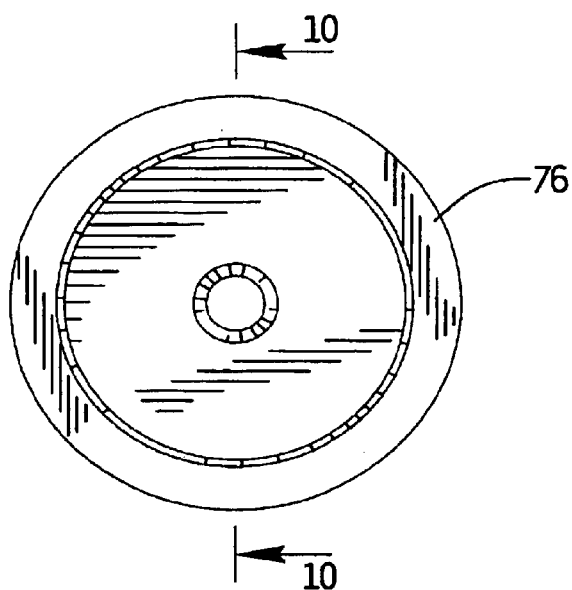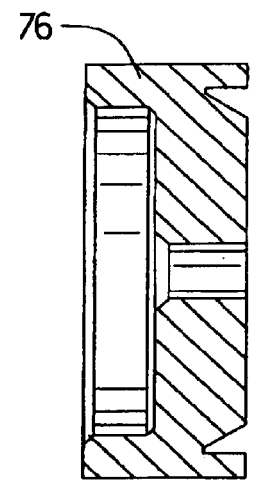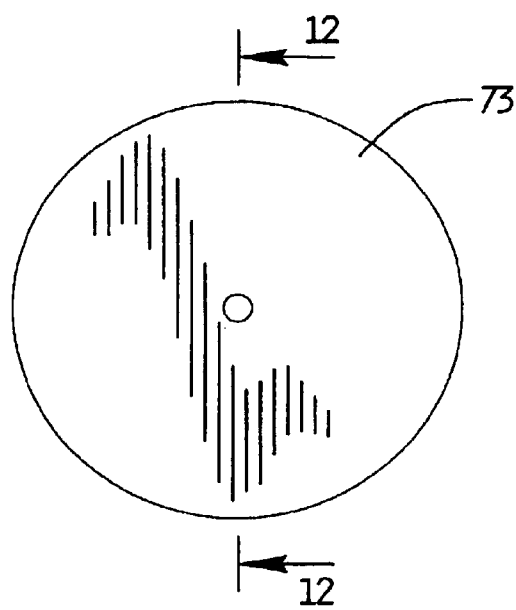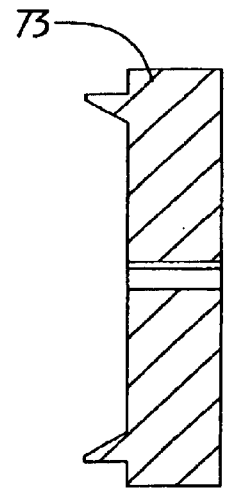
FIG_9   FIG_10   FIG_11   FIG_12

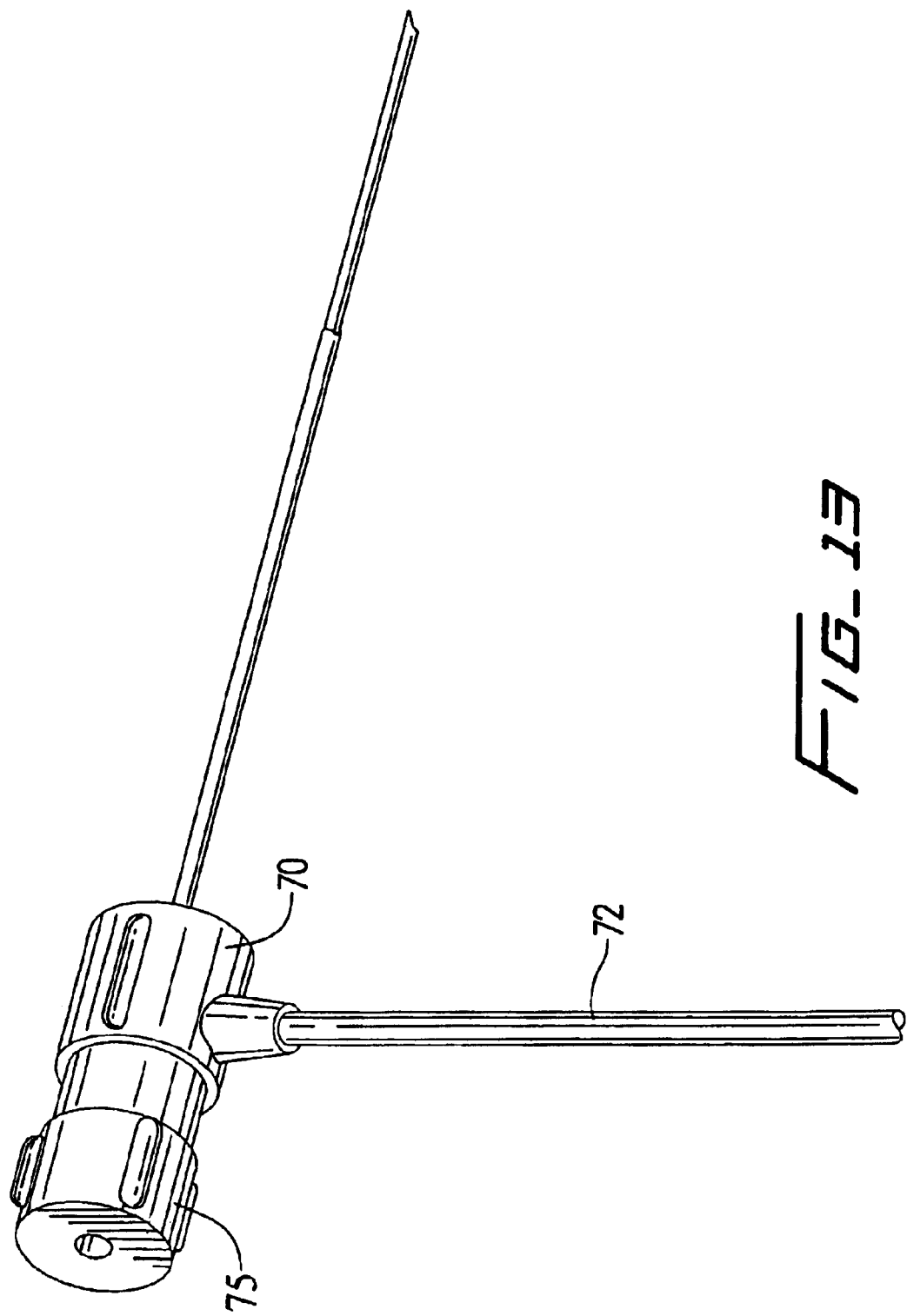

THROMBECTOMY DEVICE WITH MULTI-LAYERED ROTATIONAL WIRE

This application claims priority from provisional patent application Ser. No. 60/369,953, filed Apr. 4, 2002.

BACKGROUND

1. Technical Field

This application relates to a vascular device and more particularly to a thrombectomy device with an improved intravenous rotatable wire for clearing thrombus from dialysis grafts.

2. Background of Related Art

Hemodialysis is a well-known method of simulating renal (kidney) function by circulating blood. The kidneys are organs which function to extract water and urea, mineral salts, toxins, and other waste products from the blood with filtering units called nephrons. From the nephrons the collected waste is sent to the bladder for excretion. For patients suffering from chronic renal insufficiency, hemodialysis is life saving because it provides a machine to simulate the function of the kidneys, thereby enabling the patients to live independently between dialysis treatments.

In the hemodialysis procedure, blood is withdrawn from the patient's body and transported to a dialysis machine, also commonly referred to as a kidney machine. In the dialysis machine, toxins and other waste products diffuse through a semi-permeable membrane into a dialysis fluid closely matching the chemical composition of the blood. The filtered blood, i.e. with the waste products removed, is then returned to the patient's body.

In one approach, an arteriovenous fistula is created so a high rate of blood flows from the artery into the patient's vein. The blood is then withdrawn directly from the patient's vein (native vein fistula) providing high rates of blood flow. Since this approach requires multiple needle sticks in the vein to withdraw and return the blood, the vein can eventually be damaged beyond usability, blood clots can form and the vein can fail. Once the vein fails, it could no longer be used for access and an alternate site must be utilized.

To avoid the repetitive damage to the vein, dialysis grafts are used. These grafts, typically made of PTFE, are implanted under the patient's skin, typically in the patient's forearm, and the graft is sutured at one end to the vein (venous anastomosis) for outflow and at the other end to the artery (arterial anastomosis) for inflow. The graft is also typically a loop graft to provide greater access area. This graft, which functions as a shunt creating high blood flow from the artery to the vein, enables access to the patient's blood without having to directly puncture the vein. That is, the technician sticks the two needles into the graft to respectively withdraw and return blood to the patient, with the inlet on the arterial side for blood requiring filtration processing and the outlet on the vein side for return of processed blood from the dialysis machine.

The dialysis graft, while providing an advantageous arrangement for hemodialysis, may become inoperable after a period of time due to thrombus or clots formed as a result of the high rate of blood flow through the graft and repetitive injury at the venous anastomosis.

There have been various attempts to break up of clots and other obstructing material in the graft. One approach is through injection of thrombolytic agents such as urokinase or streptokinase. These agents, however, are expensive, require lengthier hospital procedures and run the risks of drug toxicity and bleeding complications as the clots are broken.

Other approaches to breaking up obstructions involve mechanical thrombectomy devices. U.S. Pat. No. 5,766,191 discloses a cage or basket composed of six memory wires that expand to press against the inner lumen to conform to the size and shape of the lumen. This multiple wire device is expensive and can be traumatic to the graft, possibly causing damage, since as the basket rotates at high speeds, the graft is contacted multiple times by the spinning wires. Other risks associated with the basket include the possibility of catching onto the graft itself and tearing the graft as well as catching and tearing the suture at the anastomotic site. Additionally, the basket can become filled with the clot which would then require time consuming withdrawal of the basket, cleaning the basket and reinserting it into the lumen.

U.S. Pat. No. 6,090,118 discloses a wire rotated to create a standing wave to remove thrombus. Pending U.S. patent application Ser. No. 10/113,248 filed Apr. 1, 2002 discloses a rotating wire with a substantially sinuous configuration to create a wave-like rotational device. The single wire is less atraumatic than the aforedescribed basket device since it minimizes contact with the graft wall while still effectively mechanically removing thrombotic material.

The present application is directed to improvements to the thrombectomy device of the foregoing '118 patent and the '248 application. These improvements include the attachment of the atraumatic tip to the distal tip of the rotatable wire and the construction of the rotational wire.

SUMMARY

The present invention provides improvements to the thrombectomy device disclosed in the foregoing '118 patent and '248 application having a rotating wire. More specifically, the improvement is to a thrombectomy apparatus for breaking up thrombus or other obstructive material in a lumen of a vascular graft or vessel having a flexible sheath and a wire positioned within the flexible sheath. The wire and flexible sheath of the thrombectomy apparatus are relatively movable so the wire has a first configuration and a second deployed configuration, and the wire is sinuous in configuration and assumes its sinuous configuration when in the deployed configuration and has a straighter configuration in the first configuration. The wire is operatively connected to a motor for rotation of the wire to enable peaks of the sinuous wire to contact a wall of the lumen to break up the thrombus or other obstructive material. The improvement to this thrombectomy apparatus comprises the wire being formed of an inner core formed by a plurality of twisted wires and an outer wire wound directly around the inner core, wherein a distal portion of the outer wire extends distal of the inner core and progressively tapers towards a distal end to form a tapered region.

The thrombectomy apparatus preferably further comprises a soft blunt tip affixed to the tapered region of the wire and extends distally beyond the tapered region. The soft tip is preferably flexible and made of an elastomeric material molded on the tapered region.

The tapered region of the outer wire preferably has individual coils spread apart from each other and has a hollow interior space therein, wherein the flexible polymeric tip flows to fill the spaces between the individual coils and the hollow interior space. In one embodiment, the individual coils of the wire in the tapered region are spread apart from each other by a distance approximately equal to a diameter of the wire of an individual coil.

In one embodiment, the soft tip is flexible and includes a proximate portion having a blind bore receiving the distal end of the wire and one or more swaged bands encircle the proximate portion of the flexible tip to secure the tip on the distal end portion of the wire.

Preferably, the plurality of twisted wires of the inner core are wound in a first direction and the outer wire is tightly wound directly over the inner core in a direction opposite the first direction.

In one embodiment, the outer wire forms coils with essentially no spaces between adjacent coils and the coils of the outer wire have an inner diameter approximately equal to an outer diameter of the inner core.

In one embodiment, the twisted wires of the inner core and the outer wire are composed of stainless steel, and at least some of the wires are heat treated at a temperature substantially less than 700 degrees Fahrenheit and substantially greater than 300 degrees Fahrenheit, and preferably about 500 degrees Fahrenheit, to retain the sinuous shape during rotation. The inner wires can be heat treated at a temperature and for a sufficient time that the sinuous shape is retained for at least about 5 minutes when the wire is moved through a test fixture consisting of a return bent tube having an inner diameter approximating the inner diameter of a hemodialysis shunt and slightly greater than the maximum width of the wire in the area of the sinusoidal shape, without loss of physical integrity of the wire.

BRIEF DESCRIPTION OF THE DRAWINGS

Preferred embodiment(s) of the present disclosure are described herein with reference to the drawings wherein:

FIG. 1 is a side view of the thrombectomy apparatus of the present invention having a sinuous rotational wire;

FIG. 2 is a side view of the thrombectomy apparatus of FIG. 1 with one of the housing halves removed to illustrate the internal components of the device;

FIG. 3A is an enlarged view of the detail A identified in FIG. 2;

FIG. 3B is an enlarged view of the detail B identified in FIG. 2;

FIG. 4 is a side view of the rotational wire of the apparatus of FIG. 1;

FIG. 5A is a side view of a section of the wire of FIG. 4 with a portion cut away showing the inner core and outer wire wound around the inner core;

FIG. 5B is an enlarged view of the distalmost tip of the rotational wire of FIG. 4 (detail C) showing the tapered region;

FIG. 5F is an enlarged side view of the wire of FIG. 4, with parts broken away, shown without the atraumatic tip;

FIG. 6 is an enlarged perspective view of the knob of the apparatus of FIG. 1 for moving the flexible sheath to expose the rotational wire;

FIG. 7 is a cross-sectional view of the knob of FIG. 6;

FIG. 8 is an enlarged view of the detail of FIG. 7;

FIG. 9 is a front view of the spacer of the apparatus of FIG. 1;

FIG. 10 is a cross-sectional view of the spacer taken along lines 10—10 of FIG. 9;

FIG. 11 is a front view of the seal of the apparatus of FIG. 1;

FIG. 12 is a cross-sectional view of the seal of FIG. 11; and

FIG. 13 is an enlarged perspective view of the Touhy of the apparatus of FIG. 1;

FIG. 14 is a diagrammatic side elevation of a wire in accordance with a process of manufacture.

DETAILED DESCRIPTION OF PREFERRED EMBODIMENTS

Figure 5C:
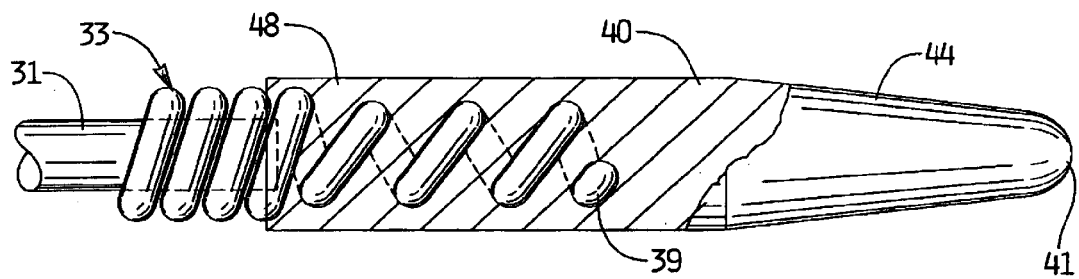
FIG. 5C is an enlarged side view, with parts broken away, of the distalmost tip of the wire with the atraumatic tip attached.
Figure 5D:
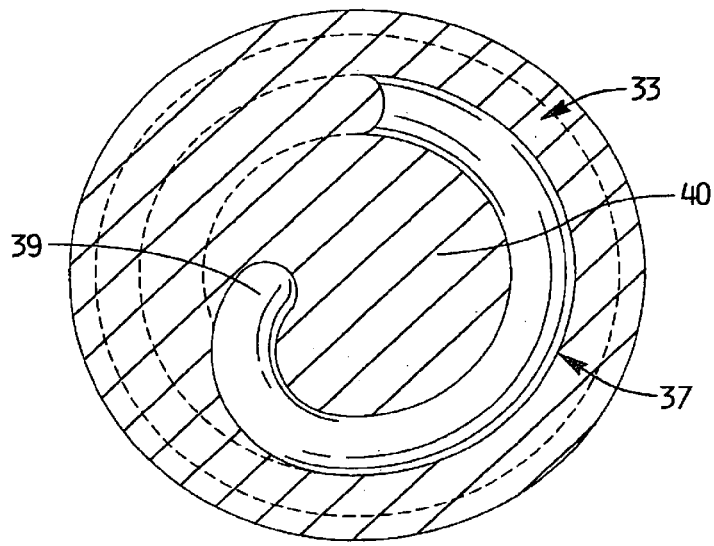
FIG. 5D is a distal end view of the wire with parts broken away.

Referring now in detail to the drawings where like reference numerals identify similar or like components throughout the several views, FIGS. 1 and 2 illustrate the thrombectomy apparatus of the present invention. Apparatus 10 has a housing 12 composed of two housing halves, a flexible catheter (tube or sheath) 20 extending from a distal end 14 of housing 12, and a rotational thrombectomy wire 30. One of the housing halves is removed in FIG. 2 to illustrate the internal components of the apparatus 10.

Wire 30 is sinuous in configuration, having a substantially linear region extending through most if its length, from a proximal region through an intermediate region until distal region 36. At the distal region 36, wire 30 has a first arcuate region 34 facing a first direction (upwardly as viewed in the orientation of FIG. 1) and a second arcuate region 38 facing a second opposite direction (downwardly as viewed in the orientation of FIG. 1). Thus, as shown, the wire 30 assumes a shape resembling a sine curve.

The distal tip 37 of wire 30 is slightly curved as it continues the "sine curve." Distal tip 37 progressively tapers toward the distalmost end 39 (see FIG. 5B). The pitch of the tapered tip 37 is constant; however, it is greater than the rest of the wire 30 which is close-wound. This open-wind and narrowing diameter facilitate attachment of the atraumatic tip described below.

With continued reference to FIGS. 5A–5D, and 5F, the wire 30, as shown, is composed of an inner core 31 formed of three twisted wire strands and an outer layer or coil 33 helically wound directly around the braided inner core 31, after it is formed, and soldered to the inner core 31 at the proximal and distal ends. The helically wound coil can cover the entire inner core 31, or alternately cover only the distal end. Also, as an alternative to the braided inner core 31, coil 33 can be wound around a solid core. This tightly wound inner/outer core structure enables rotation of the distal end of the wire 30 corresponding to rotation at its proximal end as torque is transmitted to the distal end. Rotation of the sinuous wire 30 results in a spiral path. The wires are preferably composed of stainless steel.

An atraumatic tip 40 (FIGS. 5C and 5E), preferably composed of rubber or 35D Pebax, a polyether block amide resin, although other elastomeric materials are also contemplated, is insert molded or otherwise attached to the distalmost tip of the wire 30 to provide the apparatus 10 with an atraumatic distal tip to prevent damage to the graft or vessel wall during rotation of the wire 30. The tip 40 is slightly more flexible and soft than the distal portion of the wire 30. By varying the nature and length of the polyether and polyamide blocks, desired hardness characteristics can be obtained, which can vary depending on the application. The end portion 44 of tip 40 can be tapered to a blunt or rounded end 41.

Figure 5E:
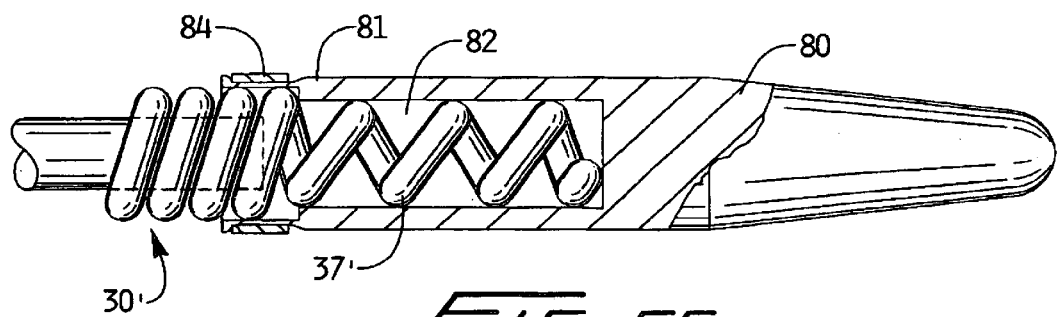
FIG. 5E is an enlarged side view, with parts broken away, of an alternate embodiment with the atraumatic tip shown attached to the wire.

The polymer tip is flexible and is preferably molded in contact with the tip by use of a heated die D, shown diagrammatically in FIGS. 5C and 5E. Molten polymer flows between adjacent coils and sets for a reliable mechanical interconnection (interlock) of the polymer tip 40 and wire 30. In the preferred embodiment, the polymer fills the otherwise empty central cavity inside the coils. Preferably the most distal four to six coils of wire 30 are spread apart lengthwise such that spaces approximately equal to the diameter of the coil wire are formed between the adjacent end coils to allow the molten polymer to flow to the interior of coils. That is, the distal end portion of the wire 30 which has the section where the pitch of the coils is changed allows the polymer to interlock between the coils and securely anchor the tip 40 onto the wire 30. This is achieved by stretching the most distal coils, thereby also decreasing the outer diameter of the wire in the area surrounded by the flexible tip 40, creating the aforedescribed taper. As shown, inner core 31 terminates proximally of the changed pitch region of the wire. As shown by way of example (see e.g. FIG. 5B), the taper occurs at the last 4.5 coils, extending a distance of about 0.080 inches in a wire having a sinuous region of about 1.64 inches. Other dimensions are also contemplated.

As shown, the spread apart and pitched end coils preferably are of reduced outside diameter, as compared to the tightly wound end coils positioned proximally therefrom. Thus the spread apart coils will be covered by a greater thickness of the polymer material, reducing the likelihood that flexing of the tip 40 will result in penetration by the inclined coils or by the extreme distal end. The proximal portion 48 of the polymer tip 18 can be of a diameter slightly greater than the diameter of the tightly wound portion of the wire.

The extreme distal end 39 of the wire of the last coil is turned inward and flattened or blunted to decrease the possibility of the polymer tip being cut, penetrated, or broken in this area.

In the alternate embodiment of FIG. 5E, the polymeric tip 80 is preformed with a blind bore or cavity 82 at its proximal portion 81, sized to receive the distal end portion 37' of the wire 30'. Once inserted over the wire, the preformed tip 80 could be secured by one or more swaged bands 84.

The flexible catheter (tube) 20 forms a slidable sheath to compress the sinuous wire 30 during delivery. That is, when the sheath 20 is in the advanced position, the curved regions of the wire 30 are compressed so the wire 30 (including the distal region 36) is contained in the sheath 20 in a substantially straight or linear configuration. This covering of the wire 30 facilitates insertion and manipulation through an introducer sheath. When the flexible sheath (tube) 20 is retracted to the position of FIG. 1 by proximal axial movement of knob 22, the distal region 36 of the wire 30 is exposed to enable the wire 30 to return to its pre-formed sinuous configuration shown in FIG. 1. The wire 30 is preferably composed of stainless steel which is pre-formed by a heat treating process to the curved configuration and returns to this position when released from the sheath 20.

Knob 22 (FIGS. 2 and 6–8) extends from distal end 14 of housing 12 and has a gripping region 26 and a shaft 28, with a lumen 27 extending therethrough. Flexible sheath 20 is attached within knob 22 such that sliding movement of knob 22 slides the flexible tube 20. Additionally, due to their attachment, knob 22 can be rotated to rotate the flexible sheath 20 for positioning of the wire 30 when deployed. Strain relief 23 extends from knob 22 and receives sheath 20.

The proximal tabs 24 of the knob 22 (FIGS. 6 and 7) twist into the threads (not shown) of the Touhy 70 to retain the sheath 20 in a retracted position to maintain the wire 30 in the exposed position. The tabs 24 also snap into a groove in the housing 12, adjacent the distal end 14, to retain the sheath in the distal position to maintain the wire in the non-deployed covered position. Although the flexible sheath 20 is shown as slidable with the wire 30 fixed axially, alternatively, the wire can be axially slidable with the sheath stationary, or both the wire and sheath can be slidable. In any case, relative movement of the wire 30 and sheath 20 will enable the wire 30 to be exposed to assume the configuration described below to enable removal of obstructions from the vascular conduit, i.e. the vascular graft or the vessel wall. Lumen 27 of knob 22 tapers in a distal direction into grip portion 26 and then at transition region 29, progressively increases in diameter from transition region 29 towards the distal end.

With reference to FIGS. 2, 3A and 3B, the internal components of apparatus 10 will now be described. Contained within housing 12 are a motor 60 and a battery 62 (two batteries are shown although one battery can also be used) which is contained within battery cassette 63. Membrane switch 64 is electrically connected by ribbon cable 68 to connector plug (male connector) 65. Connector plug 65 is connected to connector pin (female connector) 66 which is connected to the negative terminal of motor 60 via wire 63. Wire 67 electrically connects female connector 66 to the negative terminal of battery 62; wire 69 connects the positive terminal of battery 62 to the positive terminal of motor 60.

Activation of switch 64 activates motor 60 to rotate wire 30 to perform the thrombectomy procedure. That is, motor 60 rotates wire 30 by rotating support tube 39. As can be appreciated with reference to FIG. 1, the structure includes motor gear 83, drive belt 87, and chuck or gear shaft 85 positioned over speed reducing gear 81 which reduces the rotational speed (rpms) of the wire 30. Support tube 39 is bent inside gear shaft 85 by insertion of a crimping tool through slot 86 in chuck 85 to bend it into a U-shape.

Wire 30 is operatively connected to motor 60 via support tube 39 which is preferably composed of metal. Touhy 70 having extension arm 72 is positioned within housing 12 and has a lumen communicating with the lumen of flexible sheath 20. Fluids, such a imaging dye can be injected through arm 72, flowing through flexible sheath 20, between wire 30 and the inner wall of the sheath 20, and exiting distal opening to flow into the graft or vessel. This imaging dye provides an indication of flow through the graft. Touhy 70 contains a conventional silicone gasket or washer 76 (see also FIGS. 11 and 12) which is compressed when tightened to provide a seal to prevent back flow of fluid around the support tube 39. An additional sealing structure is provided in the form of a disk shaped spacer 73 (see FIGS. 9 and 10). The silicone gasket compresses the disk spacer 73 against the Touhy 70. The disk spacer 73 is on top of the silicone gasket 76 and compresses the silicone gasket 76 into the Touhy 70. Threaded cap 75 of Touhy 70 (FIG. 13) clamps down on the Touhy 70 to compress the washer 73 and spacer 76.

Turning now to one method of manufacture of the wire wherein the core is inserted into the bore of the wound outer coil, in prior methods of forming the wire into a wave shape, the three-strand core was looped as illustrated in FIG. 14 and then heat treated at 700 degrees Fahrenheit for 15 minutes for a stress relief cycle. After heat treatment, the core was pulled through a hypotube (internal diameter of about 0.041–0.043 inches) to relax the shape into the sinuous form. Heat treating prior to pulling the core was required for wave shape formation.

To improve the strength of the wire and reduce the tendency of the wire to unwind during rotation, a second heat treatment at 700 degrees for 15 minutes was conducted, but it decreased the time to failure. It was discovered that if the core wire and outer coil were wound in opposite directions, particularly with the core being wound in the direction opposite the intended rotational direction, and if the formed wave wire was heat treated once at 500 degrees F. for 15 minutes, an unexpected performance was obtained as compared to the original proposed wire, regardless of whether or not the wave shape was formed by pulling a looped wire through a hypotube or otherwise. When tested in zone 2 (the most extreme testing condition), fatigue life was increased by 2 to 3 times, while integrity of the wave shape was maintained. In comparison, with no heat treatment, or heat treatment at temperatures as high as 300 degrees F., the wave shape was lost prematurely.

Thus, in this embodiment of manufacture, the core strands are composed of stainless steel, such as 304 V hyten of a diameter of approximately 0.006 inch, and are twisted in a first direction opposite the direction of rotation of the driving member resulting in a core diameter of approximately 0.017 to 0.018 inch. After formation, the sinuous configuration is formed with two coplanar half loops extending outward about 1.5 to 2.0 mm from the center line. It is heat treated at a temperature substantially less than 700 degrees F. and substantially greater than 300 degrees F., and preferably at about 500 degrees F. The core is fitted within the outer coil which is a single strand wound in the opposite direction and with essentially no spaces between adjacent coils. The inner diameter of the outer coil is approximately equal to the outer diameter of the inner coil and the material is preferably stainless steel, such as 304V spring temper stainless steel, of a diameter of about 0.009 inch. The outer coil is secured in position over the core, preferably by welding at the proximal and distal ends. The outer coil forms the wave shape of the core.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. In a thrombectomy apparatus for breaking up thrombus or other obstructive material in a lumen of a vascular graft or vessel, the apparatus having a flexible sheath and a wire positioned within the flexible sheath, the wire and flexible sheath being relatively movable so the wire has a first configuration and a second deployed configuration, the wire being sinuous in configuration and assuming its sinuous configuration when in the deployed configuration and having a straighter configuration in the first configuration, the wire being operatively connected to a motor for rotation of the wire to enable peaks of the sinuous wire to contact a wall of the lumen to break up the thrombus or other obstructive material, the improvement comprising the wire formed of an inner core formed by a plurality of twisted wires and an outer wire wound directly around the inner core, a distal portion of the outer wire extending distal of the inner core and progressively tapering towards a distal end to form a tapered region.

2. The thrombectomy apparatus of claim 1, further comprising a soft blunt tip affixed to the tapered region of the outer wire.

3. The thrombectomy apparatus of claim 2, wherein the soft tip is composed of an elastomeric material molded on the distal end of the wire over the tapered region.

4. The thrombectomy apparatus of claim 1, wherein the tapered region of the outer wire has individual coils spread apart from each other and has a hollow interior space therein, and the apparatus further comprises a flexible tip filling the spaces between the individual coils and the hollow interior space, the flexible tip extending distally beyond the tapered region of the wire and having a blunt distal end.

5. The thrombectomy apparatus of claim 1, wherein the tapered region of the wire has spread apart individual coils forming spaces therebetween such that molding of a flexible polymeric tip in contact with the spread apart coils enables the polymer to flow between and to the interior of the coils, and the polymer is allowed to set to form the flexible tip on the tapered region of the wire.

6. The thrombectomy apparatus of claim 2, wherein the tapered region of the outer wire includes individual coils spread apart forming spaces therebetween and the soft blunt tip is flexible and fills the spaces for a secure mechanical interlock of the tip on the tapered region of the wire.

7. The thrombectomy apparatus of claim 1, wherein the outer wire has individual coils and the individual coils in the tapered region are spread apart from each other by a distance approximately equal to a diameter of the wire of an individual coil.

8. The thrombectomy apparatus of claim 3, wherein the tapered region of the outer wire includes individual coils spread apart forming spaces therebetween and the outer wire includes a tightly wound proximate section.

9. The thrombectomy apparatus of claim 2, wherein the soft tip is flexible and includes a proximate portion having a blind bore receiving the distal end of the wire and secured thereon.

10. The thrombectomy apparatus of claim 9, further comprising one or more swaged bands encircling the proximate portion of the tip to secure the tip on the distal end of the wire.

11. The thrombectomy apparatus of claim 1, wherein the plurality of twisted wires of the inner core are wound in a first direction and the outer wire is tightly wound directly over the inner core in a direction opposite the first direction.

12. The thrombectomy apparatus of claim 1, wherein the outer wire forms coils with essentially no spaces between adjacent coils and the coils of the outer wire have an inner diameter approximately equal to an outer diameter of the inner core.

13. The thrombectomy apparatus of claim 1, wherein the twisted wires of the inner core and the outer wire are composed of stainless steel, and at least some of the wires are heat treated at a temperature substantially less than 700 degrees Fahrenheit and substantially greater than 300 degrees Fahrenheit to retain the sinuous shape during rotation.

14. The thrombectomy apparatus of claim 13, wherein the heat treated wires are heat treated at a temperature of about 500 degrees Fahrenheit.

15. The thrombectomy apparatus of claim 1, wherein the inner wires are heat treated at a temperature and for a sufficient time that the sinuous shape is retained for at least about 5 minutes when the wire is moved through a test fixture consisting of a return bent tube having an inner diameter approximating the inner diameter of a hemodialysis shunt and slightly greater than the maximum width of the wire in the area of the sinusoidal shape, without loss of physical integrity of the wire.

* * * * *